United States Patent
Bouwman et al.

(10) Patent No.: US 8,884,042 B2
(45) Date of Patent: Nov. 11, 2014

(54) HYDROGENATION OF FATTY ACIDS USING A PROMOTED SUPPORTED NICKEL CATALYST

(75) Inventors: Hermanus Johannes Bouwman, Huizen (NL); Robert Johan Andreas Maria Terörde, Maarn (NL)

(73) Assignee: BASF Corporation, Florham Park, NJ (US)

( * ) Notice: Subject to any disclaimer, the term of this patent is extended or adjusted under 35 U.S.C. 154(b) by 250 days.

(21) Appl. No.: 13/642,617

(22) PCT Filed: Apr. 21, 2011

(86) PCT No.: PCT/NL2011/050276
§ 371 (c)(1),
(2), (4) Date: Jan. 2, 2013

(87) PCT Pub. No.: WO2011/133037
PCT Pub. Date: Oct. 27, 2011

(65) Prior Publication Data
US 2013/0109875 A1 May 2, 2013

(30) Foreign Application Priority Data
Apr. 22, 2010 (EP) .................................... 10160791

(51) Int. Cl.
| | | |
|---|---|---|
| *C07C 51/36* | (2006.01) | |
| *C11C 3/12* | (2006.01) | |
| *B01J 21/08* | (2006.01) | |
| *B01J 23/72* | (2006.01) | |
| *B01J 23/755* | (2006.01) | |
| *B01J 23/78* | (2006.01) | |
| *B01J 33/00* | (2006.01) | |
| *B01J 35/02* | (2006.01) | |
| *B01J 37/03* | (2006.01) | |
| *B01J 37/18* | (2006.01) | |

(52) U.S. Cl.
CPC ................. *C11C 3/123* (2013.01); *B01J 21/08* (2013.01); *B01J 23/72* (2013.01); *B01J 23/755* (2013.01); *B01J 23/78* (2013.01); *B01J 33/00* (2013.01); *B01J 35/023* (2013.01); *B01J 37/03* (2013.01); *B01J 37/033* (2013.01); *B01J 37/035* (2013.01); *B01J 37/038* (2013.01); *B01J 37/18* (2013.01); *C07C 51/36* (2013.01)
USPC ............ 554/146; 554/124; 554/141; 554/147

(58) Field of Classification Search
CPC ...................................................... C11C 3/123
See application file for complete search history.

(56) References Cited

U.S. PATENT DOCUMENTS

| | | | |
|---|---|---|---|
| 2,320,063 A | | 5/1943 | Borkowski et al. |
| 3,743,662 A | * | 7/1973 | Eurlings et al. ............... 554/146 |
| 4,048,116 A | | 9/1977 | Voges et al. |
| 4,133,822 A | | 1/1979 | Hasman et al. |
| 4,251,394 A | | 2/1981 | Carter et al. |
| 5,493,037 A | | 2/1996 | Henderson |
| 6,054,627 A | | 4/2000 | Thakur et al. |
| 6,080,699 A | | 6/2000 | Pohl |

FOREIGN PATENT DOCUMENTS

| | | |
|---|---|---|
| DE | 767901 | 10/1954 |
| DE | 19611132 | 9/1997 |
| EP | 0572081 | 12/1993 |
| GB | 578102 | 6/1946 |
| GB | 1122398 | 8/1968 |
| GB | 1312963 | 4/1973 |
| GB | 1574389 | 9/1980 |
| WO | WO-2004/035204 | 4/2004 |

OTHER PUBLICATIONS

"International Search Report in PCT/NL2011/050276", mailed on Aug. 8, 2011, 3 pgs.
"Machine Translation of DE767901", 3 pgs, Oct. 25, 1954.
EP Search Report in EP 10 16 0791, dated Oct. 28, 2010, 7 pgs.

* cited by examiner

*Primary Examiner* — Yate K Cutliff
(74) *Attorney, Agent, or Firm* — Melanie L. Brown

(57) ABSTRACT

The invention is directed to a process for the hydrogenation of unsaturated fatty acids to produce saturated fatty acids, said process comprising hydrogenating the unsaturated fatty acid in the presence of hydrogen and a supported nickel catalyst, said supported nickel catalyst comprising an oxidic support, 5 to 80 wt. % of nickel, calculated as atomic nickel on the weight of the catalyst, 0.1 to 10 wt. % of a copper promoter, calculated as atomic copper on the weight of the catalyst and 1 to 10 wt. % of a group II metal, calculated as metallic oxide on the weight of the catalyst.

16 Claims, No Drawings

HYDROGENATION OF FATTY ACIDS USING A PROMOTED SUPPORTED NICKEL CATALYST

CROSS-REFERENCE TO RELATED APPLICATIONS

This application is the National Stage entry of PCT/NL2011/050276, filed on Apr. 21, 2011, which claims priority to European Patent application number 10160791.9, filed on Apr. 22, 2010, both of which are incorporated herein by reference in their entireties.

FIELD

The invention is directed to the hydrogenation of unsaturated fatty acids to produce saturated fatty acids, said process comprising hydrogenating the unsaturated fatty acid in the presence of hydrogen and a supported nickel catalyst.

BACKGROUND

Supported metal catalysts are known, and their use in numerous reactions, including the hydrogenation of unsaturated fatty materials, such as oils or fatty acids has been described extensively in the literature. Supported nickel catalysts have been utilized in various hydrogenation processes where low IV (iodine value) fatty products are desired. A low IV is obtained when the product is completely or essentially completely saturated.

U.S. Pat. No. 6,054,627 describes a catalyst comprising the major amount of the oxides of copper or zinc and at least one other metal to be used in hydrogenation reactions. U.S. Pat. No. 5,493,037 describes a catalyst comprising nickel, silica, alumina and one clay mineral binder used in fixed bed hydrogenation of fatty acid. Contents of 10-50 wt. % of nickel are mentioned, without specifying how the weight percentage is defined. WO-A-2004/035204 describes a nickel catalyst with magnesium promoter used for hydrogenating unsaturated organic compounds. Contents of 51-80 wt. % of nickel, determined in the reduced catalyst, are disclosed. U.S. Pat. No. 4,048,116 describes an unsupported nickel catalyst also comprising of copper and manganese and optionally molybdenum for hydrogenation of acetylene alcohols. U.S. Pat. No. 4,133,822 describes a process for hydrogenation of unsaturated fatty acid using a nickel catalyst also comprising of a copper chromite adjunct catalyst. GB-A-1 312 963 describes a copper and nickel containing catalyst suitable for the hydrogenation of oils.

EP-A-0 572 081, GB-A-1 574 389, DE-C-767 901, U.S. Pat. No. 2,320,063 and U.S. Pat. No. 4,251,394 describe supported nickel and copper catalysts used for the hydrogenation of oils and fats. GB-A-578 102 describes a promoted hydrobleaching catalyst comprising nickel, iron and copper.

SUMMARY

One aspect of the invention relates to a process for the hydrogenation of unsaturated fatty acids to produce saturated fatty acids. In one or more embodiments, said process comprises hydrogenating the unsaturated fatty acid in the presence of hydrogen and a supported nickel catalyst, said supported nickel catalyst comprising an oxidic support, 5 to 80 wt. % of nickel, calculated as atomic nickel on the weight of the catalyst, 0.1 to 10 wt. % of a copper promoter, calculated as atomic copper on the weight of the catalyst and 1 to 10 wt. % of a group II metal, calculated as metallic oxide on the weight of the catalyst.

DETAILED DESCRIPTION

Fatty acid hydrogenations can be accomplished generally in a slurry phase with a powdered catalyst or in a fixed bed with a shaped catalyst. Nickel catalysts are often used for fatty acid hydrogenation reactions applications. However, such catalysts may exhibit a relatively fast deactivation caused by extensive crystallite growth as a result of Ostwald ripening. Also major amounts of the nickel dissolve in the fatty acid feedstock under reaction conditions. This deactivation rate should be minimized in order for such a catalyst to be economical in mentioned processes.

The present invention relates to the use of a nickel on silica catalyst which has been promoted with copper and a group II metal for the hydrogenation of (natural oil derived) fatty acids, which is a feedstock for oleochemical processes.

The invention accordingly is directed to a process for the hydrogenation of unsaturated fatty acids to produce saturated fatty acids, said process comprising hydrogenating the unsaturated fatty acid in the presence of hydrogen and a supported nickel catalyst, said supported nickel catalyst comprising an oxidic support, 5 to 80 wt. % of nickel, calculated as atomic nickel on the weight of the catalyst, 0.1 to 10 wt. % of a copper promoter, calculated as atomic copper on the weight of the catalyst and 1 to 10 wt. % of a group II metal, calculated as metallic oxide on the weight of the catalyst. All weight % referred to herein are based on the weight of the reduced catalyst, unless otherwise indicated.

Surprisingly nickel catalysts promoted with copper deactivate slower under reaction conditions. The actual mechanism for this is effect is not known, but it is assumed that formation of nickel-copper alloy crystallites, which are less sensitive for dissolution/re-precipitation during the hydrogenation reaction, is responsible.

The present invention can be applied for the fatty acid hydrogenation to low iodine values, i.e. in the hydrogenation of (poly)unsaturated fatty acids to produce saturated fatty acids.

Fatty acids hydrogenated in accordance with the present invention are carboxylic acids with a branched or unbranched aliphatic chain preferably consisting of $C_6$ to $C_{36}$, more preferably $C_{16}$ to $C_{24}$.

Preferably the catalyst used in the present invention comprises 25 to 80 wt. % of nickel, more preferably >30 wt. %, and even more preferably >60 wt. %, calculated as atomic nickel on the weight of the catalyst.

The copper promoter content of said catalyst comprises preferably 0.5 to 5 wt. %, more preferably 1.5 to 5 wt. %, calculated as atomic copper on the weight of the catalyst.

As support it is preferred to use one or more oxides, whereby of the oxides silica, alumina, silica-alumina, titania, zirconia and combinations thereof are preferred. More in particular it is preferred to use silica as the said oxidic support material. However, other supports are not excluded, for example carbon, zeolites and clay materials.

The most preferred supported catalyst used in the present invention comprises 1 to 90.0 wt. % silica, preferably 5 to 70 wt. % and more preferably >10 to <65 wt. %, calculated on the weight of the catalyst.

The group II metal may be selected from magnesium, barium, calcium and strontium. Preferably the group II metal is magnesium. Preferably said catalyst comprises 1 to 10 wt. % magnesium, calculated as MgO on the weight of the catalyst.

In a preferred embodiment the supported nickel catalyst comprises >10 wt. % silica, on the weight of the catalyst, >60 wt. % of nickel, calculated as atomic nickel on the weight of the catalyst, and 1.5 to 5 wt. % of a copper promoter, calculated as atomic copper on the weight of the catalyst and 1 to 10 wt. % of magnesium, calculated as MgO on the weight of the catalyst.

The catalyst may be coated with a protective layer, e.g. a fatty substance such as hardened soy bean fat, hardened palm oil fat, hardened sun flower oil fat or a combination thereof, which may serve to avoid oxidation of (parts of) the catalyst. A method for applying a suitable fatty is known in generally known in the art, and may be based on WO 2004/035204. This may for example be done by blending a (reduced) catalyst powder into the molten coating material (such as the molten fat) and subsequently solidifying the resulting suspension to form flakes or droplets of coated catalyst particles.

The melting temperature of the protective material with which the catalyst is coated is preferably less than the temperature at which the hydrogenation is carried out, in order to facilitate dissolution of the protective material at the beginning of a hydrogenation process. In particular, when the catalyst is used in a slurry process, the protective coating will preferably dissolve in the feedstock. Else, the coating may be removed from the process, shortly before using the catalyst in a hydrogenation process. The coating may very suitably be removed by contacting the catalyst with a solvent, such as a feedstock, preferably at a temperature higher than the melting point of the coating fat.

The average particle size of the catalyst is preferably from 0.1 to 50 μm. These particles may be shaped (extruded, tabletted etc) into larger particles, especially suitable for fixed bed applications.

The nickel surface area of the catalyst (in active form) will preferably have hydrogen adsorption capacity (HAC) ranging from 20 to 50 ml $H_2$/g catalyst, more preferably from 28 to 36 ml $H_2$/g catalyst. The nickel surface area as used herein is the value as can be determined by hydrogen desorption, after in situ reduction with hydrogen (50 ml/min) for 2 hours at 400° C. in a Micromeretics AutoChem 2920 chemisorption analyzer. Following in situ reduction the sample is cooled to −75° C. with liquid nitrogen. Subsequently, the hydrogen adsorption capacity (HAC) of the sample is determined by measuring the amount of hydrogen that desorbs during heating in a flow of argon (20 ml/min) from −75 to 700° C.

The BET surface area preferably is about 200 to about 450 $m^2$/g catalyst, more preferably about 250 to about 400 $m^2$/g catalyst. The BET surface area as used herein is the value that can be measured by determining the amount of nitrogen adsorbed at 77 K and P/Po of approximately 0.3 and assuming a nitrogen cross sectional area of 16.2 $Å^2$, after degassing the catalyst sample at 180° C.

In a preferred embodiment, the catalyst is made from a catalyst precursor that is prepared by co-precipitation, of which it will be clear to the skilled professional how to choose suitable method conditions. In a co-precipitation method according to the invention nickel, silica copper and a group II metal are precipitated together (i.e. without forming intermediate precipitates of only one or some of the components). In such a method, a nickel source, a silica source, a copper source and a group II metal source may be mixed in a liquid (e.g. water or an aqueous solution) to form a precipitate (a catalyst precursor), comprising all said components. It is possible to feed the various aqueous solutions of the component precursors simultaneously to a reactor vessel, to do this sequentially and/or to provide an amount of liquid in the reactor at the beginning and/or to add a precipitant, such as an alkaline compound at some stage. In an alternative one can use deposition-precipitation using a preformed support.

The catalyst precursor is activated by reducing at least part of the nickel and copper content of the catalyst precursor, and optionally the catalyst precursor is calcined before being reduced.

The nickel, silica, copper and a group II metal sources may be chosen from sources commonly used to prepare catalysts.

Suitable nickel and copper, and other metal sources include metal salts such as the nitrates, acetates, sulfates, chlorides, etc, most preferably chlorides. Preferably the metal source is a solution of any of these salts.

Suitable silica sources include water glass, sodium silicate and colloidal silica. Preferably the silica source is a solution or suspension of any of these components.

The processes of the present invention are performed preferably at a temperature of from 100 to 400° C. Acceptable pressures for the present invention range from 3 to 150 bar.

The process according to the invention has been found to be particularly suitable for the hydrogenation of unsaturated fatty acids to produce saturated fatty acids of low iodine values.

The invention is now elucidated on the basis of some examples, which are not intended to limit the scope of the invention.

EXAMPLES

Reference Example 1000 ml of a solution of nickel chloride (95 g nickel per liter and magnesium chloride (5 g magnesium per liter) in water and 1000 ml of a solution sodium metasilicate (61 g $Na_2SiO_3.5H_2O$ per liter) and sodium carbonate (183 g per liter) were simultaneously and at the same rate pumped into a well-stirred 4-liter precipitation vessel at a temperature of 80° C. The pH of the slurry was 7.2 and after about 1 hour the precipitation was completed.

After washing of the precipitate with approx. 30 liter of water, the precursor of the catalyst formed was filtered and dried in an oven at 110° C. The catalyst was activated with hydrogen.

Example-1

1000 ml of a solution of nickel chloride (92 g nickel per liter), copper chloride (3 g copper per liter) and magnesium chloride (5 g magnesium per liter) in water and 1000 ml of a solution sodium metasilicate (61 g $Na_2SiO_3.5H_2O$ per liter) and sodium carbonate (183 g per liter) were simultaneously and at the same rate pumped into a well-stirred 4-liter precipitation vessel at a temperature of 80° C. The pH of the slurry was 7.2 and after about 1 hour the precipitation was completed.

After washing of the precipitate with approx. 30 liter of water, the precursor of the catalyst formed was filtered and dried in an oven at 110° C. The catalyst was activated with hydrogen.

Example-2

1000 ml of a solution of nickel chloride (90 g nickel per liter), copper chloride (5 g copper per liter) and magnesium chloride (5 g magnesium per liter) in water and 1000 ml of a solution sodium metasilicate (61 g Na$_2$SiO$_3$.5H$_2$O per liter) and sodium carbonate (183 g per liter) were simultaneously and at the same rate pumped into a well-stirred 4-liter precipitation vessel at a temperature of 80° C. The pH of the slurry was 7.1 and after about 1 hour the precipitation was completed.

After washing of the precipitate with approx. 30 liter of water, the precursor of the catalyst formed was filtered and dried in an oven at 110° C. The catalyst was activated with hydrogen.

ACTIVITY TEST

The activity of the reference nickel catalyst and the two examples of a copper promoted catalyst, example-1 and example-2, was determined by hydrogenating 500 g tallow fatty acid having an iodine value of 56 at 200° C. at a hydrogen pressure of 20 bars with an amount of catalyst corresponding to 0.032 wt. % nickel. The time to IV-4 of example-1 and example-2 was compared with the reference catalyst under the same conditions. Also the end IV after 90 minutes was determined for example-1 and example-2 and compared with the reference catalyst.

| Examples | Cu atomic wt. % | Time to IV-4 (min) | IV after 90 min |
|---|---|---|---|
| Reference | 0 | 51 | 1.86 |
| Example-1 | 2.3 | 42.5 | 1.64 |
| Example-2 | 3.9 | 42 | 1.32 |

As can be seen from the above results, the catalysts of the present invention which contains the copper promoter are more effective in the hydrogenation of the fatty acid (shorter reaction time and lower iodine value).

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for the hydrogenation of unsaturated fatty acids to produce saturated fatty acids, said process comprising hydrogenating the unsaturated fatty acid in the presence of hydrogen and a supported nickel catalyst, said supported nickel catalyst comprising an oxidic support, 5 to 80 wt. % of nickel, calculated as atomic nickel on the weight of the catalyst, 0.1 to 10 wt. % of a copper promoter, calculated as atomic copper on the weight of the catalyst and 1 to 10 wt. % of a group II metal, calculated as metallic oxide on the weight of the catalyst.

2. The process of claim 1, wherein the catalyst comprises 25 to 80 wt. % of nickel, preferably >30 wt. %, and even more preferably >60 wt. %, calculated as atomic nickel on the weight of the catalyst.

3. The process of claim 1, wherein the catalyst comprises 0.5 to 5 wt. % of a copper promoter, preferably 1.5 to 5 wt. %, calculated as atomic copper on the weight of the catalyst.

4. The process of claim 1, wherein the support is an oxidic support, the support preferably selected from silica, alumina, silica-alumina, titania, zirconia and combinations thereof.

5. The process of claim 4, wherein the oxidic support material of said catalyst is silica.

6. The process of claim 1, wherein said catalyst comprises 1 to 90 wt. % silica, preferably 5 to 70 wt. %, more preferably >10 to <65 wt. %, calculated on the weight of the catalyst.

7. The process of claim 1, wherein the catalyst has an average particle size of 0.1 to 50 μm.

8. The process of claim 1, wherein the group II metal is selected from magnesium, barium, calcium and strontium.

9. The process of claim 8, wherein the group II metal is magnesium.

10. The process of claim 1, wherein the catalyst is suspended in droplets, wherein the droplets form a protective coating layer effective in preventing oxidation of the catalyst, said protective coating layer preferably comprises of a fatty substance.

11. The process of claim 1, wherein the hydrogenation is carried out at a temperature between 100 and 400° C.

12. The process of claim 1, wherein the hydrogenation is carried out at a hydrogen pressure between 3 and 150 bar.

13. The process of claim 1, wherein the supported nickel catalyst comprises >10 wt. % silica, calculated on the weight of the catalyst, >60 wt. % of nickel, calculated as atomic nickel on the weight of the catalyst, 1.5 to 5 wt. % of a copper promoter, calculated as atomic copper on the weight of the catalyst and 1 to 10 wt. % of magnesium, calculated as MgO on the weight of the catalyst.

14. The process of claim 13, wherein the catalyst is suspended in droplets, wherein the droplets form a protective coating layer effective in preventing oxidation of the catalyst, said protective coating layer preferably comprises of a fatty substance.

15. The process of claim 1, wherein the hydrogenation is carried out in a fatty acid slurry containing the catalyst.

16. The process of claim 14, wherein the hydrogenation is carried out in a fatty acid slurry containing the catalyst.

* * * * *